United States Patent [19]

Belmonte-Martinez et al.

[11] Patent Number: 5,525,601
[45] Date of Patent: Jun. 11, 1996

[54] COMPOSITION FOR TREATING OCULAR PAIN

[75] Inventors: Carlos Belmonte-Martinez; Roberto Gallego-Fernandez, both of Alicante; Miguel A. Pozo-Garcia, Madrid; Juana Gallar-Martinez, Alicante, all of Spain

[73] Assignee: Universidad de Alicante, Alicante, Spain

[21] Appl. No.: 434,949

[22] Filed: May 4, 1995

Related U.S. Application Data

[63] Continuation of Ser. No. 855,018, Jul. 7, 1993, abandoned.

[30] Foreign Application Priority Data

Sep. 7, 1990 [ES] Spain ...................... 9002335

[51] Int. Cl.$^6$ .................. A61K 31/54; A61K 31/44
[52] U.S. Cl. .................. 514/222.2; 514/356; 514/912
[58] Field of Search ............... 514/222.2, 356, 514/912

[56] References Cited

U.S. PATENT DOCUMENTS

| | | | |
|---|---|---|---|
| 4,552,695 | 11/1985 | Igarashi ................... | 260/239.3 |
| 4,562,075 | 12/1985 | Rajadhyaksha ............ | 514/788 |
| 4,981,871 | 1/1991 | Abelson .................... | 514/523 |
| 5,202,130 | 4/1993 | Grant ....................... | 424/617 |

FOREIGN PATENT DOCUMENTS

WOA19006123 6/1990 WIPO.

OTHER PUBLICATIONS

Gunderson, C., Management of the Migraine Patient, American Family Physician, vol. 33, No. 1, 1986, pp. 137–143.

J. Walton, Diffuse exercise–induced muscle pain of undetermined cause relieved by verapamil, The Lancet, 1981, p. 993.

Pfister R. et al., Polymorphonuclear Leukocytic Inhibition by Citrate, Other Metal Chelators, and Trifluoperazine, Eye Res. Labs, Birmingham, AL, Invest. Ophthalmol. Visual Sci. (USA) Aug. 1984, 8:955–970.

Bignall J. et al., Aspirin, nifedipine and cataract, The Surgery, Newport, Dyfed U.K., Lancet, Eng., 1986, 2/8497 (42–43).

Pozo M. et al., Blockadge by Calcium Antagonists of Chemical Excitation and Sensitization of Polymodal Nociceptors in the Cat's Cornea, J. of Physiol., 1992, 450, pp. 179–189.

Bussey, H. and R. Talbert, Promising Uses of Calcium-Channel Blocking Agnets, Pharmacotherapy (1984) 4:137–143.

Cat's Cornea, J. of Physiol., 1992, 450, pp. 179–189.

Moses, R. ed. Adler's Physiology of the Eye, The C.V. Mosby Co. St. Louis, 1987, pp. 44; 56–58.

Goodman and Gilman's The Pharmacological Basis of Therapeutics, Pergamon Press, New York, pp. 774–783, 1990.

Primary Examiner—Zohreh Fay
Attorney, Agent, or Firm—Wolf, Greenfield & Sacks

[57] ABSTRACT

The invention relates to the use of a calcium channel blocking agent for the manufacture of a medicament for alleviating pain, such as ocular pain. Particular calcium channel blocking agents that can be used in accordance with the invention are diltiazem, verapamil, nifedipine, nicardipine, and nimodipine.

20 Claims, 1 Drawing Sheet

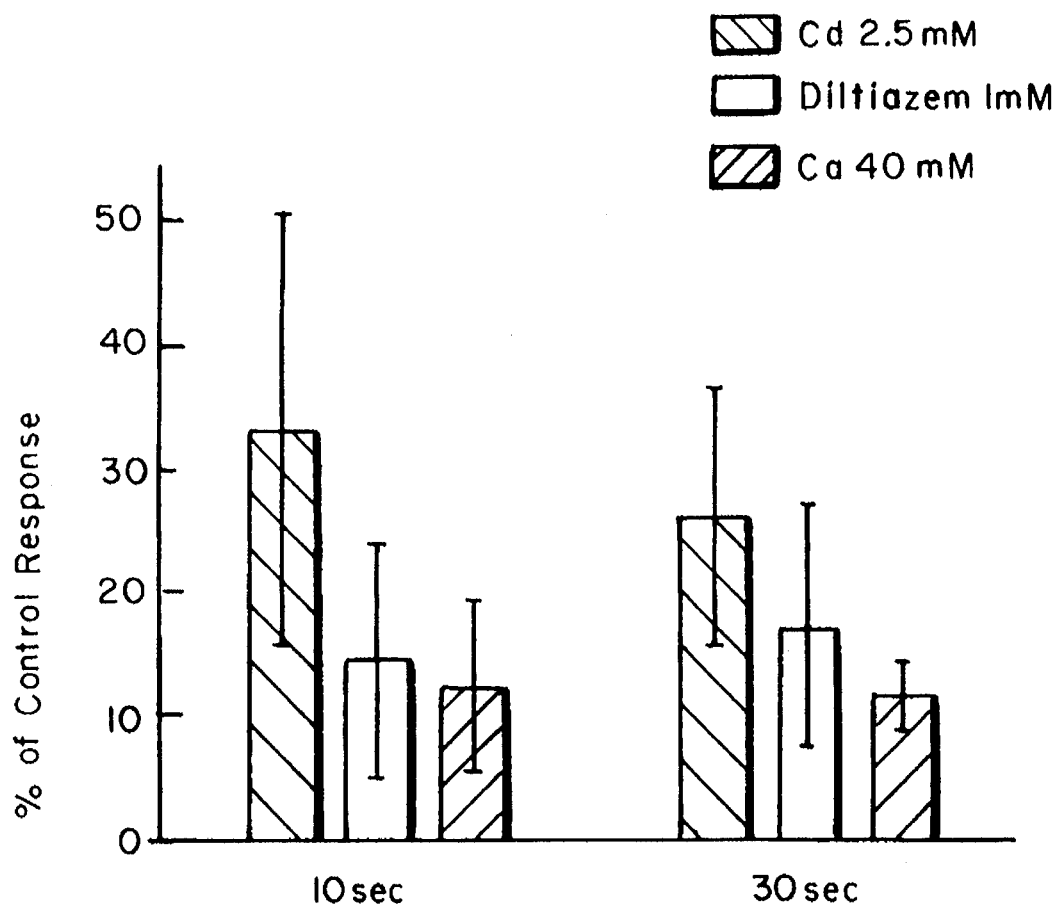

COMPOSITION FOR TREATING OCULAR PAIN

This application is a continuation of application Ser. No. 07/855,018, filed Jul. 7, 1993, now abandoned.

FIELD OF THE INVENTION

This invention relates to the topical application of calcium channel blocking agents for treating ocular pain and neurogenic inflammation and compositions useful for such application.

BACKGROUND OF THE ART

Pain is a well known phenomenon as an indicator of injury or tissue damage due to inflammation, ischemia, mechanical or other irritation [Juan, H., Prostaglandins as Mediators of Pain, *Gen. Pharmacy*, 9.403–409 (1978)].

The first step leading to the sensation of pain is the activation of nociceptive primary afferents by intense thermal, mechanical or chemical stimuli. Indirect studies of nociceptive transduction (activation) indicate that it involves chemical mediators that are released or synthesized in response to tissue damage [Fields, H. and Levine, J., Pain-Mechanisms and Management, *Western Medical J.* 141, 347–357 (1984)]. These chemical mediators include lactic acid, hypertonic saline, histamine, 5-hydroxytryptamine, potassium chloride, acetylcholine, purines, bradykinin and substance P which are referred to as algesic agents (Juan, H., Supra). In recent years it has been shown that prostaglandins and leukotrines can contribute to the activation of primary afferent nociceptors (Fields, H. and Levine, J., Supra). Prostaglandins are uniquely distinguished from the other chemical mediators in that they induce a state of hyperalgesia by elevating the sensitivity of pain receptors to other painful or algasic stimuli.

The stimulation of primary afferents leads to action potentials in their axons which propagate to the spinal cord. In addition, excited primary afferents release nuropeptides (substance P, calciotonin-gene-related peptide, neurokinin A) at their peripheral terminals. Neuropeptides enhance inflammatory reactions in the injured tissue, contributing to vasodilation, edema, and increased vascular permeability; this phenomenon is called 'neurogenic inflammation'.

In the spinal cord, the nociceptors enter the gray matter of the superficial dorsal horn to synapse on nerve cells contributing to pain-transmission pathways such as the spinothalamic and spinoreticulothalamic tracts which terminate in two separate regions in the thalamus. The two thalamic regions in turn project to different cortical sites (Fields, J. and Levina, J., Supra).

The pain transmitting and modulating system depicted so far depends on numerous chemical moieties for its integrated function [Fine, P. and Hare, B., The Pathways and Mechanisms of Pain and Analgesis, L A Review and Clinical Perspective, *Hospital Formul.* 20, 972–985 (1985)].

Anesthetics block neuronal transmission and affect sensation as well as pain. Analgesics act by interfering with the activity of chemical mediators without affecting sensory input.

According to Remington's Pharmaceutical Sciences, 17th Ed., analgesics can be classified as falling into at least three loose groups: 1) the opiate-based (narcotic) analgesics; 2) the non-opiate analgesics; and 3) analgesics and antipyretics.

The opiate-based analgesics include opium derived alkaloids, including morphine, codeine, and their various derivatives, opiate antagonists, the several morphine derivatives which have morphine antagonist activity, but have analgesic activity.

Since these narcotic type drugs are addictive, a number of nonaddictive, non-opiate analgesics have been developed in an attempt to produce an analgesic which is highly efficient but not addictive.

In the third broad category, the analgesics and antipyretics, are the salicylates and acetamide-containing compounds and the so-called non-steroidal anti-inflammatory drugs. They are non-addictive pain killers.

As to their mode of action, drugs that block perception of pain may be said to act either centrally (such as narcotics) or peripherally.

Centrally acting narcotic drugs are true analgesics because they can relieve pain regardless of the etiology.

The non-steroidal anti-inflammatory agents (NSAIAs) have been described as peripheral pain relievers. It was further suggested that the analgesic properties of these drugs are independent of their antiedema or anti-inflammatory actions [Capetola et al., Supra].

The action of NSAIAs as pain relievers is associated with the biosynthesis of prostanoids.

Inflammation or trauma and resultant tissue injuries cause the release of arachidonic acid which is degraded by cyclooxygenase and lipoxygenase. The cyclo-oxygenase pathway leads to the synthesis of prostaglandin $E_2$ ($PGE_2$) and other mediators. $PGE_2$ release increases the cyclic AMP and ionic calcium levels at the nociceptor membrane resulting in a lowered activation threshold, resulting in the relay to the central nervous system of augmented pain perception (hyperalgesia) [Capetola et al., Peripheral Antialgesics: A Review, *J. Clin. Pharmacol.* 23, 545–556 (1983)]. Inhibitors of prostaglandin synthesis, such as NSAIAs, act avoiding the sensitizing effects of prostaglandins on nociceptive endings and therefore, the decrease in pain threshold.

In animal models and human studies non-steroidal anti-inflammatory agents have been shown to inhibit inflammatory pain [Terasawa et al., Analgesic effect of topically applied pranoprofen-gel, *Nippon Yakurigaku Zasshi* 86(6), 433–440 (1985); Cherevatov et al., Topical Use of Rheumon-Gel in combined treatment of patients with rheumatoid arthritis, *Ter. Arkh.* (USSR), 59(12) 100–102 (1987); and Kyuki et al., Anti-inflammatory Effect of diclofenac-sodium ointment (cream) in topical application, *Jpn. K. Pharmacol,* 33(1), 121–123 (February 1983)].

Ophthalmic applications of various NSAIAs are also known, including the utilization of their anti-inflammatory properties for control of various ocular inflammations. [See Anderson et al., Disposition of topical flurbiprofen in normal and aphakic rabbit eyes, *Arch. Ophthalmol,* 100, 642–645 (1982); Duflin et al., Inhibitors of surgically induced miosis, *Ophthalmol,* 86, 966–979 (1983); and Keates and McGowan, Clinical trial of flurbiprofen to maintain pupillary dilation during cataract surgery, *Ann. Ophthalmol,* 16(10), 919–921 (1984).

NSAIAs have been used for the treatment of non-inflammatory, localized pain, such as non-inflammatory ocular pain. See U.S. patent application Ser. No. 07/585,664, filed on Sep. 20, 1990 in the of Gwon.

Calcium channel blockers or antagonists are compounds which delay or prevent the cardiac contracture which is believed to be caused by an accumulation of intracellular calcium under ischaemic conditions. Calcium overload, during ischaemia, can have a number of additional adverse effects which would further compromise the ischaemic myocardium. These include less efficient use of oxygen for ATP production, activation of mitochondrial fatty acid oxidation, and possibly, promotion of cell necrosis. Thus, the compounds are useful in the treatment or prevention of cardiac conditions, such as angina pectoris, cardiac arrhythmias, heart attacks and cardiac hypertrophy. The compounds also possess vasodilator activity and are thus useful as antihypertensives and for the treatment of coronary vasospasm. Calcium channel blockers of the verapamil type are known to lower elevated intraocular pressure. See U.S. Pat. No. 4,981,871. Calcium channel blockers are not suggested as useful for treating pain, including ocular pain.

SUMMARY OF THE INVENTION

As will be appreciated from the above, various analgesics, anesthetics, etc. have been used to treat ocular pain. However, nowhere is it suggested that compounds having calcium channel blocking activity may be used to treat ocular pain.

The present invention is based on the unexpected finding that compounds having calcium channel blocking activity efficiently relieve ocular pain, including ocular pain and inflammation associated with corneal injuries.

The use of a topical composition, including a calcium channel blocking agent, for the relief of eye pain offers several benefits over the use of systemic agents because of the decreased systemic absorption, which may decrease side-effects, and increased ocular absorption that can increase efficacy.

Moreover, certain calcium channel blockers alleviate ocular pain associated with chemical stimuli but do not affect mechanical stimuli. As sustained discharges in nociceptive fibers are maintained by chemical mediators released by injured tissues, this invention permits the attenuation of pain elicited by these mediators without interfering with sensitivity to mechanical stimuli. In addition, decrease of responsiveness of nociceptive terminals by calcium channel blockers reduce neurogenic inflammation resulting in the release of neuropeptides by excited nociceptors.

Accordingly, the present invention relates to a method for treating ocular pain in a mammal afflicted by such pain, which method comprises applying to the eye of said mammal an effective amount of a calcium channel blocking agent in a pharmaceutically acceptable vehicle.

DETAILED DESCRIPTION OF THE INVENTION

The present invention relates to the use of calcium channel blocking agents for the treatment of ocular pain.

The term "calcium channel blocking agent" or "compound having calcium channel blocking activity" or "calcium channel antagonist" is used to define compounds which are known to prevent or delay the cardiac contracture which is caused by an accumulation of intracellular calcium.

Suitable calcium channel blockers include verapamil, nifedipine, diltiazem, fostedil and the various derivatives, including the analogues and homologues, thereof, having calcium channel blocking activity. Verapamil and the like are disclosed in U.S. Pat. Nos. 3,261,859; 4,593,042 and 4,681,970. Nifedipine is disclosed in U.S. Pat. No. 3,485,847 and is a 1,4-dihydropyridine in which the 2 and 6 positions are substituted by methyl groups, the 4 position by 2-nitrophenyl and the 3 and 5 positions by carboxylic acid methyl ester groups. Similar compounds are disclosed in U.S. Pat. Nos. 3,455,945; 3,325,505; and 3,441,468 to Loew and 3,470,297 and 3,511,837 to Bossert, which introduced variations in the 4-substituent. U.S. Pat. Nos. 3,905,970 to Bossert, et al. and 3,985,758 to Marakami, et al. introduced certain mono- or dialkylamino-alkylene and nitrogen-containing heterocyclic alkylene groups into one or both of the 3,5 ester groups. U.S. Pat. Nos. 4,307,103 and 4,393,070 to Sato disclose 1,4-dihydropyridines in which the 2 position is not substituted by alkyl, but instead is substituted with cyano, formyl or certain other substituents and the ester group in the 3 position may contain various substituted alkyl groups including substituted alkylaminoalkyl, heterocyclic aminoalkyl and aroylaminoalkyl, including phthalimidoethyl. U.S. Pat. No. 4,448,964 to Muto, et al., discloses compounds in which the 3-position ester group contains certain substituted piperidinyl alkylene groups.

Other pyridine compounds having calcium channel blocking activity are disclosed in U.S. Pat. Nos. 4,652,573; 4,755,512; 4,791,117; 4,794,187; 4,814,455; 4,829,076; 4,871,745; 4,895,846 and 4,912,223.

Diltiazem and the like are disclosed in U.S. Pat. Nos. 3,562,257 and 4,552,695.

The structures of the preferred calcium channel blockers utilized in the method and compositions of this invention are as follows:

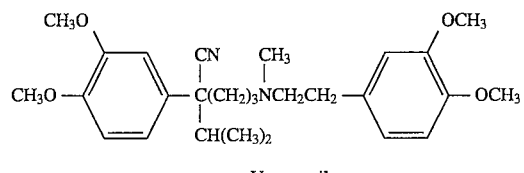

Verapamil

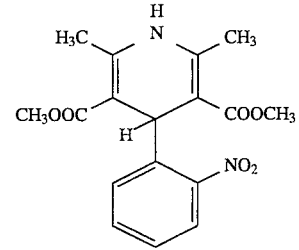

Nifedipine

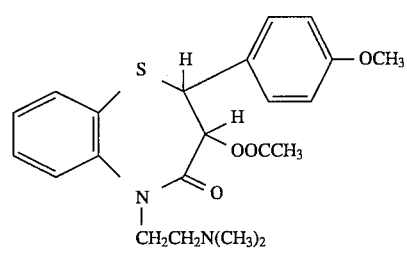

Diltiazem

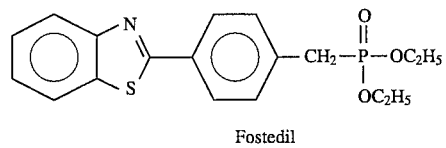

Fostedil

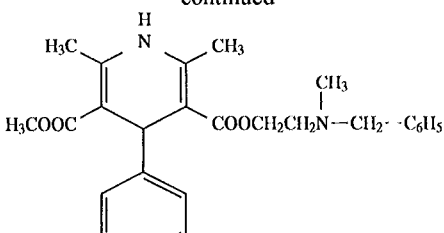

Nicardipine

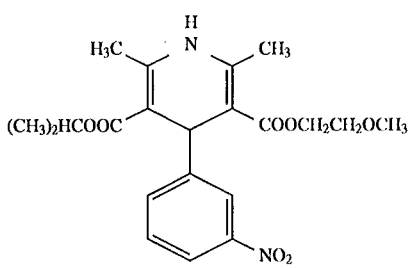

Nimodipine

This listing represents the well known calcium channel blocking agents, i.e., those marketed or tested for human use. But the mere listing of these particular, presently marketed or tested calcium channel blocking agents, is not intended to limit the scope of the compounds which might be used in practicing the present invention. Any calcium channel blocking agent can be used in accordance with this invention.

Calcium channel blocking activity varies substantially from compound to compound. Generally, when administered systemically, calcium channel blocking agents are effective in a wide range of concentrations. For example, diltiazem tablets contain 30 to 120 mg of active ingredient per tablet.

An effective dose, when it comes to topical, ocular pain, is a matter of similarly broad therapeutically effective dose requirements. This figure is one controlled by a number of factors: the inherent activity of the drug itself; the vehicle in which it is administered, primarily topical delivery being anticipated; the size of the area to be treated; and the intensity of the pain. Exact dosing data have not been determined for all compounds within the scope of this invention. But it is anticipated that a topical formulation having between 0.001% and 1.0% (weight/volume) of a calcium channel blocking agent will provide relief from ocular pain. The determination of the effective dose for any selected compound is well within the skill of an ordinary skilled physician.

In the practice of this invention, calcium channel blocking agents may be administered in any manner which will deliver the drug directly to the locale of the pain to be treated. It is anticipated that this will be by application to the immediate area of distress. For example, the drug could be applied topically, or by subcutaneous injection or by some similar means which delivers the drug directly to the affected area. It is not intended that this invention be practiced by administering the drug in such a way as to insure that it gets to the central nervous system. In fact, that would defeat the whole purpose of this invention which is focused on treating the pain at its source.

For ophthalmic application, preferably solutions are prepared typically containing from about 0.001% to about 1.0% of active ingredient, and a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and/or penetration enhancers.

The preferred vehicle that may be used in the ophthalmic solutions of the present invention is purified water, more preferably a physiological saline solution. Additional suitable vehicles include but are not restricted to, viscosity agents such as polyvinyl alcohol, povidone, hydroxypropyl methyl cellulose, poloxamers, carboxymethyl cellulose, carbomer and hydroxyethyl cellulose.

Preferred preservatives that may be used in the ophthalmic formulations of the present invention include, but are not limited to, benzalkonium chloride, chlorobutanol, thimerosal, phenylmercuric acetate and phenylmercuric nitrate.

Penetration enhancers may, for example, be surface active agents; certain organic solvents, such as dimethylsulfoxide and other sulfoxides, dimethylacetamide and pyrrolidone; certain amides of heterocyclic amines, glycols (e.g., propylene glycol); propylene carbonate; oleic acid; alkyl amines and derivatives; various cationic, anionic, nonionic, and amphoteric surface active agents; and the like.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting ph may be used so long as the resulting preparation is ophthalmically acceptable. Accordingly, buffers include acetate buffers, citrate buffers, phosphate buffers and borate buffers for ophthalmic use.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The invention is further illustrated by the following non-limiting examples.

BRIEF DESCRIPTION OF THE DRAWINGS

FIG. 1 shows the effects of acidic stimulation when the cornea has been treated previously with 2.5 mMCd$^{2+}$ or with 1 mm diltiazem.

EXAMPLE 1

A clinical study is performed to compare the analgesic effect of topically administered diltiazem and placebo following radial keratotomy surgery. One hundred and twenty-four male and female subjects, 21 to 45 years of age, who undergo routine, elective, unilateral radial keratotomy for the correction of myopia participated in the study, and diltiazem was administered as a 0.03% ophthalmic solution.

Each subject receives one drop of the assigned study medication every four hours while awake one day prior to surgery and again every 20 minutes for the two hours just before surgery. Each subject then undergoes unilateral radial keratotomy. Following surgery, each subject receives one drop of the study medication in the operated eye every four hours while awake for 14 consecutive days. Postoperative examinations occur at days 1, 3, 7 and 14.

Efficacy is assessed by evaluation of pain intensity, pain relief, subjective global analgesic efficacy. Symptoms of ocular inflammation (burning/stinging, tearing, etc.) are also recorded.

The results of this study show statistically significantly greater pain relief at hours 2, 3 and 4 in the diltiazem group over the group treated with placebo. This appears to suggest that diltiazem, administered preoperatively, might block the perception of pain.

EXAMPLE 2

A 54 year old woman, hard contact lens wearer, has a one day history of sharp shooting pain in both eyes. Diltiazem was prescribed as a sole treatment of pain. On instillation of the medication, the patient reports relief of pain for approximately two and a half hours. Upon recurrence of pain, a second dose of diltiazem provides pain relief.

EXAMPLE 3

A 32 year old female patient with a history of gas-permeable contact lens wear has a two-to-three day history of pain in her left eye. The patient is treated with diltiazem for pain. The patient reports relief of pain for two hours.

EXAMPLE 4

An experiment was carried out in adult cats anaesthetized with sodium pantobarbitone (Nembutal, 40 mgfkg, I.P.). In order to keep a deep arreflexic state during the experiment, a dilute solution of the anaesthetic (15 mg/ml) was infused through the radial vein. The animal was secured to a stereotaxic frame, tracheotomized and left to breathe spontaneously. End-tidal $CO_2$ was continuously monitored to remain around 4%. Rectal temperature was maintained between 36°–38° C. with a heating blanket.

The superior and lateral walls of the orbital cavity were removed and the extrinsic muscles of the eye resetted to expose the ciliary nerves. A ciliary nerve was carefully dissected under a binocular microscope and placed on Ag—AgCl electrodes. Conventional electrophysiological equipment, consisting of a.c. amplifier with modifiable filters, oscilloscope and loudspeaker, was used to record impulse discharges. Conduction velocities were calculated from the delay of the evoked response to suprathreshold electric shocks (0.1–0.5 ms, 0.5–3 mA), applied with a pair of polished silver electrodes on the limbus or the cornea. Mechanical stimulation was performed manually, using a wet, fine brush. To measure mechanical threshold, a calibrated Cochet-Bonnet esthesiometer was employed. The receptive field was mapped using the tip of the esthesiometer adjusted at suprathreshold values [Belmonte and Giraldez, *J. Physiol*, 321,355 (1981)].

Chemical substances were assayed by applying with a pipette on the receptive field 60 microliters of the test solution for 60 s. After treatment, the area was washed repeatedly with balanced saline. Concentrations of chemicals used were as follows: Acetic acid, 10 mmol.l$^{-1}$ dissolved in distilled water, citric acid. Impulse discharges were stored on an FM tape for later off-line computer analysis. Taking the first impulse in the response as zero time, mean discharge rates during the initial 10s of the response and during the complete 30 s period of stimulus application were calculated. Frequency values were expressed in impulses. The experimental protocol was as follows: initial identification of the unit was made by mechanical stimulation of the cornea, sliding a wet, fine brush on the corneal surface. The receptive field was then mapped and after a pause of at least 3 min, force threshold was estimated with the esthesiometer, starting from the lowest intensity (0.1 mN) and increasing the force exerted until a consistent response was evoked in different points of the receptive area. Conduction latencies were measured afterwards by electrical stimulation of the center of the receptive field and of the limbus. After at least 5 min, a drop of a citric acid solution at pH 5.5 was applied on the corneal surface for 30s, to determine chemosensitivity of the recorded unit. A 3–5 min period was allowed between chemical stimulation with each stimulating solution. A total of 14 fibers was employed. Average extracorneal conduction velocity was 8.1±1.6 m/s (mean+S.E, n=13) and 0.7±0.3 at the intracorneal course. Mechanical threshold was 1.47±0.32 mN (n=14).

In five polymodal fibers, the receptive field was flushed with a saline solution at pH 7.5 applied every 20 s during 2 min. Immediately afterwards, a single (60 µl) dose of saline at pH 5.5 was applied and maintained for 1 min on the corneal surface before being washed away with saline at pH 7.5. After a 3 min pause, the procedure was repeated by applying this time a conditioning solution at pH 6.5 every 20 s during 2 min, ;and then a drop of saline at pH 5.5. Impulse activity was recorded throughout the experiment.

In eight fibers the response to a pH 4.5 solution applied during 30 s was initially ascertained. Then, 60 µl of a 2 mM $Cd^{2+}$ solution at pH 7.3 was applied with 15 s intervals during 5 min. At the end of this period, a 2 mM $Cd^{2+}$ solution of pH 4.5 was applied as the acidic stimulus. Mechanical responsiveness and threshold were also measured. If the response to acid was still present, application of 2 mM $Cd^{2+}$ at pH 7.3 every 15 s was resumed during another 5 min period. When a reduction or a suppression of the impulse discharge to acid was detected, washing of the cornea with saline at pH 7.3 was performed at 1 min intervals and the response to a citric acid solution of pH 4.5 explored every 5 min until partial or total recover was achieved. The same experimental procedure was used to assay effects of diltiazem 1 mM in six separate corneal polymodal units.

The results are reported in FIG. 1. In this Figure the effects of acidic; stimulation when the cornea has been treated previously with 2.5 mM $Cd^{2+}$ or with 1 mM diltiazem. A reduction of the response to a high $(H^+)_0$ stimulating solution (pH 4.5) was obtained after treatment with calcium blocking agents. In contrast, impulse discharges elicited by mechanical stimulation remained unchanged as did the mechanical threshold of the fibers. The effect of $Ca^{2+}$ blockers was reversible and after washing out of the cornea for a variable time (20 to 40 min) the response to acid was fully recovered. Verapamil (100 µM) failed to modify excitatory effects of acid on corneal nociceptors. FIG. 1 also illustrates the influence of increased $(Ca^{2+})_0$. A reduction of the amplitude of the firing response to a pH 4.5 citric acid solution was obtained after exposure of the cornea to 40 mM $Ca^{2+}$ whereas mechanical sensitivity remained unaltered. The effect was reversible after washing of the cornea for 5 min with the control solution. Increases in $(H^+)_0$ occur during tissue injury and hypoxia and may contribute to stimulation and/or sensitization of nociceptors and thus to pain. The fact that responses of a single fiber to acid could be blocked pharmacologically with $Ca^{2+}$ antagonists without interfering with mechanical responsiveness opens therapeutical possibilities in the management of pain of peripheral origin.

EXAMPLE 5

This experiment was carried out in adult cats. Nerve activity was recorded either from nerve filaments containing several cornea/sensory fibers or from single corneal afferent units identified as polymodal nociceptors. Corneal receptive fields innervated by active fibers were stimulated mechanically with a Cochet-Bonnet esthesiometer and chemically with 10 mM acetic acid. Verapamil (1 mM) or nifedipine (1 mM) were applied topically 5 min later. Mechanical and chemical stimulation were repeated twice with 5 min intervals; then, the cornea was washed for 30 min and sensitivity to acid and to mechanical stimulation again tested. Number of impulses during 60s following application of acid was counted. The effect of drugs was expressed as percent reduction of the control response to acid.

Verapamil, assayed in three single units produced in two of them an increase in ongoing firing frequency (from 0.01 to 0.10 and from 0.04 to 0.15) and no changes in the remaining unit. It reduced in all fibers the response to acid to an average value of 19.7% of control. Mechanical threshold increased in two of the units and remained unaltered in the third. A reduction of size of the receptive field was noticed in all instances after verapamil.

Nifedipine was tested in three filaments displaying multiunit discharges; in one of them, application of nifedipine produced a clear increase of ongoing activity; the other two responded to the administration of the drug either with a small and short-lasting frequency increase or with no change in spontaneous activity. Discharges evoked by subsequent applications of acid were markedly reduced by nifedipine in the three filaments explored, to an average value of 15% of control. Responses to mechanical stimulation persisted after nifedipine. Nevertheless, the presence of many different units in the recording precluded a determination of threshold; also, the possibility that a portion of the fibers were inactivated by the drug cannot be excluded in these experimental conditions.

From these preliminary experiments it can be concluded that nifedipine and verapamil reduce chemical responsiveness of nociceptors as occurs with diltiazem. However, in contrast to diltiazem, both drugs, at the doses employed, show a brief discharge of impulses upon instillation. Also, a certain degree of inactivation of mechanical responsiveness was observed with verapamil.

EXAMPLE 6

This experiment is directed to demonstrate that calcium blockers reduce ocular pain and inflammatory reactions in rabbits. Two types of experiments are done:

Group 1

In a first group of experiments, forty-one (41) adult albino rabbits are employed. Animals received in both eyes 60 µl of 1% capsaicin (8.5% Tween 80, 1.5% ethanol in isotonic saline) with a 5 min interval between eyes. Number of wiping movements, blepharospasm (resistance to opening of the eye), pupil diameter, conjunctival vasodilation and size of palpebral opening were measured (−, +, ++, +++, ++++) at pre-established times: immediately after capsaicin and 15 min, 60 min, 180 min and 280 min after instillation of the drug. Also, a subjective evaluation of the discomfort shown by the animal to manipulations of the eye was made. At 285 min, 10 mg/kg of fluorescein were injected into the marginal vein of the ear; the rabbits were anesthetized 15 min later (ketamine, 30 mg/kg and xylacine, 3 mg/kg, i.v.) and aqueous humor was obtained by paracentesis of the anterior chamber. Fluorescein content was measured with a fluorimeter (Perkin Elmer, LS-5); Aqueous humor proteins were determined by the Bradford method. In addition to capsaicin, the animals received 60 µl of a solution of diltiazem in one eye and of the vehicle (124 mM NaCl, 5 mM KCl, pH=7.3 adjusted with 20 mM HEPES) in the contralateral eye. In other cases (control eyes), the vehicle was applied in both eyes. Treatment with diltiazem was administered as:

1) A single dose of diltiazem 1 mM (10 rabbits), 2.8 mM (9 rabbits) and 10 mM (9 rabbits), applied 15 min before capsaicin.

2) Repeated doses of diltiazem 1 mM, applied 15 min before and 120 min and 240 min after capsaicin (5 rabbits).

3) A single dose of the vehicle in both eyes (8 rabbits), 15 min before capsaicin.

Diltiazem administration and measurement of irritation parameters were made by independent investigators, that ignored the treatment given to or received by the explored animal.

Group 2

Forty-two pigmented rabbits are used for this experiment. Animals were exposed to ultraviolet radiation (254 nm for 5 min), pupil diameter, epithelial debris, epithelial stipping, epithelial granules, epithelial haze, epithelial exfoliation, stromal haze, stromal opacities, conjunctival vasodilation, sluggishness of pupillary response and bleariness were explored with the slit lamp 8 and 24 hours after exposure to UV radiation, according to Pitts et al. (Invest Ophthalmol Vis Sci. 16:932, 1977). One eye of each animal was treated with 60 µl of topical diltiazem while the other received the vehicle, at the following times and doses:

1) Treatment with a single dose of diltiazem 1 mM, 15 min before UV exposure.

2) Treatment with a single dose of diltiazem 1 mM, 5 min after UV exposure.

3) Treatment with 1 mM diltiazem administered 15 min before and 7 h, 15 h and 22 h after UV radiation.

4) Treatment with a single dose of 10 mM dialtiazem, 15 min before UV exposure.

As in Group 1, diltiazem administration and measurements were made by independent investigators.

Results

Topical capsaicin produced an immediate motor response composed by scratching movements with the forepaw (wipes) directed to the eye; the animal closed totally or partially the eye (blepharospasm) and maintained afterwards a certain degree of palpebral closure. Miosis and conjunctival hyperemia were also present. These phenomena lasted for about 1–1.5 h. Statistical comparisons (paired t-test) were made between the eye that was pre-treated with diltiazem and the contralateral, vehicle-treated eyes. Significant differences in motor responses (number of wiping movements, blepharospasm and palpebral opening) were noticed at the three doses tested. Miosis tends to be less marked in the eye treated with diltiazem than in contralateral eyes but differences are conclusive. Conjunctival hyperemia is reduced significantly by diltiazem. The subjective evaluation of discomfort also shows a significantly reduced value in eyes treated with diltiazem. Significant differences in fluorescein or protein content in aqueous humor were noticed between diltiazem-treated and control eyes.

Ultraviolet radiation produced an inflammatory reaction of the anterior uvea that was not detectable at 8 hours but was clearly apparent 24 hours after exposure. In preliminary experiments we had detected that the inflamatory effect of UV radiation was more prominent in pigmented rabbits; for this reason that species was selected for this study. Differences in severity of pupillary, corneal and inflammatory reactions noticed with 1 mM diltiazem were not significant. A dose of 10 mM diltiazem improved epithelial and stromal signs of damage and conjunctival hyperemia, while the pupil was not greatly affected by the UV exposure or by diltiazem.

The results of the present experiments indicate that diltiazem, at relatively low doses (1–2.8 mM) reduced pain reactions to anterior segment irritation. This observation is in agreement with previous electrophysiological data, shoring a decrease by diltiazem of nociceptive activity evoked by acidic stimulation in corneal nociceptive afferents. At higher doses (2.8–10mM), an attenuation of conjunctival inflammatory reaction to chemical irritation of the eye was also observed. Experiments with UV radiation further support the observation that diltiazem at doses over 1.8 mM exerts an anti-inflammatory action.

For example, since the functional properties of the different types of peripheral nociceptors appear to be the same in different tissues (skin, Bessou & Perl, J. Neurophysiol. 32:1025, 1969; joints, Schaible & Schmidt, J. Neurophysiol. 54:1109, 1985; muscle, Mense, J. Physiol. 267:75, 1977; testis, Kumazawa & Mizumura, J. Physiol. 299:219, 1980; cornea, Belmonte & Giraldez, J. Physiol. 321:355, 1981; teeth, Jyvasjarvi, Kniftki & Mengel, Progress Brain Res., 74:237, 1988). The method of the present invention may be used to treat pain in other parts of the body than the eye. Moreover, certain pain will require systemic rather than topical administration and, therefore, treating pain systemically is within the scope of the present invention. Again since polymodal nociceptors of the eye, i.e., the class of nociceptive nerve terminals that respond to lesive mechanical, thermal and chemical stimuli are analogous to those found in the skin and mucosae or in the teeth, (this is not surprising, considering that these tissues share a common embryological origin). It is to be expected that the pain-attenuating effects produced by calcium channel blockers on the eye are also present in the skin and mucosae if the medication can reach the superficial nociceptive nerve endings, as will occur when penetration is enhanced by artificial means or when the mucosae or skin are damaged. The same will be true in the tooth when intradental nociceptive fibers of the dental pulp are exposed. Therefore, this invention can be extended to the local treatment of superficial pain and neurogenic inflammation of the skin and mucosae.

The foregoing description details specific formulations and methods that can be employed to practice the present invention. Having detailed specific compositions for the topical formulations of the present invention and specific instructions for their use in the treatment of ocular pain, the art skilled will well enough know how to devise other formulations and how to adapt the treatment (formulations, doses) to a special situation. Thus, however detailed the foregoing may appear in text, it should not be construed as limiting the overall scope hereof; rather, the ambit of the present invention is to be governed only by the lawful construction of the appended claims.

We claim:

1. A method for alleviating ocular surface pain in a mammalian eye comprising administering to a mammalian eye having ocular surface pain an amount of a calcium channel blocking agent effective to alleviate the ocular surface pain.

2. The method of claim 1 wherein said mammalian eye is a human eye.

3. The method of claim 1 wherein said administration is topical administration directly to said eye.

4. The method of claim 1 wherein said calcium channel blocking agent is selected from the group consisting of diltiazem, verapamil, nifedipine, fostedil, nimodipine, nicardipine and derivatives thereof.

5. The method of claim 1 wherein said calcium channel blocking agent is administered in solution in a pharmaceutically acceptable ophthalmic vehicle.

6. The method of claim 1 wherein said effective amount is from about 1 to about 10 mg per eye per day.

7. The method of claim 5 wherein said vehicle contains from about 0.01 to about 20 mg per ml of said calcium channel blocking agent.

8. The method of claim 1 wherein said pain is associated with a wound or inflammation in said eye.

9. The method of claim 1 wherein said calcium channel blocker is diltiazem.

10. The method of claim 1 wherein said calcium channel blocker is verapamil.

11. The method of claim 1 wherein said calcium channel blocker is nifedipine.

12. The method of claim 1 wherein said pain is associated with radial keratotomy.

13. The method of claim 1 wherein said pain is associated with treatment by a laser.

14. The method of claim 12 wherein said laser is an excimer laser.

15. The method of claim 1 wherein said pain is associated with corneal abrasion.

16. A method for alleviating nonvascular associated pain in a mammal comprising administering to said mammal having nonvascular associated pain an amount of a calcium channel blocking agent effective to alleviate the nonvascular associated pain.

17. The method of claim 16 wherein said calcium channel blocking agent is selected from the group consisting of diltiazem, verapamil, nifedipine, fostedil, nimodipine, nicardipine and deterivatives thereof.

18. The method of claim 16 wherein said calcium channel blocker is diltiazem.

19. The method of claim 16 wherein said calcium channel blocker is verapamil.

20. The method of claim 16 wherein said calcium channel blocker is nifedipine.

* * * * *